US010123969B2

(12) United States Patent
Thorne et al.

(10) Patent No.: US 10,123,969 B2
(45) Date of Patent: Nov. 13, 2018

(54) OSMOTIC ENHANCEMENT OF DRUG/THERAPEUTIC DELIVERY TO THE BRAIN FOLLOWING INFUSION OR INJECTION INTO THE CEREBROSPINAL FLUID

(71) Applicant: Wisconsin Alumni Research Foundation, Madison, WI (US)

(72) Inventors: Robert G. Thorne, Madison, WI (US); Michelle E. Pizzo, McFarland, WI (US); Daniel J. Wolak, San Francisco, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/293,925

(22) Filed: Oct. 14, 2016

(65) Prior Publication Data
US 2017/0105927 A1 Apr. 20, 2017

Related U.S. Application Data

(60) Provisional application No. 62/241,998, filed on Oct. 15, 2015.

(51) Int. Cl.
*A61K 9/00* (2006.01)
*A61K 35/545* (2015.01)
*A61K 39/395* (2006.01)
*A61K 47/26* (2006.01)
*A61K 35/12* (2015.01)
*C07K 16/00* (2006.01)
*A61K 39/00* (2006.01)

(52) U.S. Cl.
CPC .......... *A61K 9/0004* (2013.01); *A61K 9/0019* (2013.01); *A61K 9/0085* (2013.01); *A61K 35/12* (2013.01); *A61K 35/545* (2013.01); *A61K 47/26* (2013.01); *C07K 16/00* (2013.01); *A61K 2039/505* (2013.01); *A61K 2039/54* (2013.01); *C07K 2317/569* (2013.01)

(58) Field of Classification Search
None
See application file for complete search history.

(56) References Cited

U.S. PATENT DOCUMENTS

| 7,662,140 | B2 * | 2/2010 | Heruth | A61M 5/14276 |
| | | | | 604/502 |
| 8,658,203 | B2 | 2/2014 | Drummond et al. | |
| 9,044,381 | B2 | 6/2015 | Rabinow et al. | |
| 2003/0225031 | A1 | 12/2003 | Quay | |
| 2010/0221233 | A1* | 9/2010 | Borlongan | A61K 9/0019 |
| | | | | 424/93.72 |
| 2011/0158969 | A1 | 6/2011 | Chopp | |
| 2011/0318431 | A1 | 12/2011 | Gulati | |
| 2012/0003202 | A1 | 1/2012 | Calias et al. | |
| 2012/0087869 | A1* | 4/2012 | Thakker | A61K 31/711 |
| | | | | 424/9.34 |

FOREIGN PATENT DOCUMENTS

| CN | 103655584 | A | 3/2014 |
| EP | 3813420 | B1 | 6/2002 |
| KR | 1020070113088 | A | 11/2007 |
| WO | 0050058 | A1 | 8/2000 |
| WO | 2005059115 | A1 | 6/2005 |
| WO | 2012039979 | A2 | 3/2012 |

OTHER PUBLICATIONS

Calias, et al., Intrathecal Delivery of Protein Therapeutics to the Brain: A Critical Reassessment, Pharmacology & Therapeutics, 2014, 144:114-122.
Cook, et al., Intracerebroventricular Administration of Drugs, Pharmacotherapy, 2009, 29(7):832-845.
Creighton, Solubility of Mannite in Mixtures of Ethyl Alcohol and Water, Journal of the Franklin Institute, 1923, 195 (5):687-691.
Gabas, et al. Solubilities of D-xylose and D-mannose in Water-Enthanol Mixtures at 25.degree.C, Journal of Chemical & Engineering Data, 1988, 33(2):128-130.
Gonzales-Portillo, et al., Mannitol-Enhanced Delivery of Stem Cells and Their Growth Factors Across the Blood-Brain Barrier, Cell Transplant., 2014, 23:531-539.
Gray, et al., Production of Recombinant Adeno-Associated Viral Vectors and Use in In Vitro and In Vivo Administration, Curr. Protoc. Neurosci., 2011, Chapter: Unit 4.17.
Gray, et al., Global CNS Gene Delivery and Evasion of Anti-AAV Neutralizing Antibodies by Intrathecal AAV Administration in Non-Human Primates, Gene Therapy, 2013, 20(4):450-459.
Hamza, et al., A Prospective, Randomized, Single-Blinded, Head-to-Head Long-Term Outcome Study, Comparing Intrathecal (IT) Boluses with Continuous Infusion Trialing Techniques Prior to Implantation of Drug Delivery Systems . . ., Neuromodulation: Technology at the Neural Interface, 2015, 18(7):636-649.
Iliff, et al., A Paravascular Pathway Facilitates CSF Flow Through the Brain Parenchyma and the Clearance of Interstitial Solutes, Including Amyloid B, Sci. Transl. Med., 2012, 4(147):147ra111.
Iliff, et al., Brain-Wide Pathway for Waste Clearance Captured by Contrast-Enhanced MRI, Journal of Clinical Investigation, 2013, 123(3)1299-1309.

(Continued)

*Primary Examiner* — Robert A Wax
*Assistant Examiner* — William Craigo
(74) *Attorney, Agent, or Firm* — Quarles & Brady LLP

(57) ABSTRACT

A method of enhancing therapeutic/drug transport to the perivascular space of the brain of a patient is disclosed. In one embodiment, the method comprises the step of introducing a therapeutic/drug and an osmolyte of the present invention into a patient's cerebrospinal fluid (CSF), wherein the osmolyte is introduced to the CSF at a concentration of between 0.5 and 12.9 M (dependent on the solubility upper limit of the osmolyte), and wherein the therapeutic/drug delivery to the perivascular spaces of cerebral blood vessels and parenchyma of the central nervous system is facilitated by the presence of the osmolyte.

18 Claims, 10 Drawing Sheets
(8 of 10 Drawing Sheet(s) Filed in Color)

(56) References Cited

OTHER PUBLICATIONS

Jin, et al., Arsenic Trioxide Entered Cerebrospinal Fluid with the Help of Mannitol Overwhelm the Meningeal Relapse of Acute Promyelocytic Leukemia, Haematologica, 2007, 92:e82-e84.

Kaialy, et al., Freeze-Dried Mannitol for Superior Pulmonary Drug Delivery via Dry Powder Inhaler, Pharm. Res., 2013, 30:458-477.

Lochhead, et al., Rapid Transport Within Cerebral Perivascular Spaces Underlies Widespread Tracer Distribution in the Brain After Intranasal Administration, Journal of Cerebral Blood Flow & Metabolism, 2015, 35:371-381.

Needham Jr., et al., Solubility of Amino Acids in Pure Solvent Systems, Journal of Pharmaceutical Sciences, 1971, 30(4):565-567.

Park, et al., Intrathecal Trastuzumab Treatment in Patients with Breast Cancer and Leptomeningeal Carcinomatosis, Cancer Res. Treat., 2016, 48(2):843-847.

Samaranch, et al., Strong Cortical and Spinal Cord Transduction After AAV7 and AAV9 Delivery into the Cerebrospinal Fluid of Nonhuman Primates, Human Gene Therapy, 2013, 24:526-532.

Speck, et al., Osmolality-Related Effects of Injections into the Central Nervous System, Investigative Radiology, 1988, 23:S114-S117.

Temsamani, et al., Brain Drug Delivery Technologies: Novel Approaches for Transporting Therapeutics, PSTT, 2000, 3(5):155-162.

Thorne, et al., Delivery of Neurotrophic Factors to the Central Nervous System, Clinical Pharmacokinetics, 2001, 40 (12):907-946.

Thorne, et al., Diffusion of Epidermal Growth Factor in Rat Brain Extracellular Space Measured by Integrative Optical Imaging, Journal of Neurophysiology, 2004, 92:3471-3481.

Thorne, Primer on Central Nervous System Structure / Function and the Vasculature, Ventricular System and Fluids of the Brain. In: Drug Delivery to the Brain: Physiological Concepts, Methodologies and Approaches. Ed. Hammarlund-Udenaes, de Lange & Thorne. Springer, New York, 2014, pp. 685-707.

Wolak, et al., Diffusion of Macromolecules in the Brain: Implications for Drug Delivery, Mol. Pharm., 2013, 10 (5):1492-1504.

Wolak, et al., Probing the Extracellular Diffusion of Antibodies in Brain Using In Vivo Integrative Optical Imaging and Ex Vivo Fluorescence Imaging, J. Control Release, 2015, 0:78-86.

\* cited by examiner

| | Dilute agarose $D$ ($10^{-8}$ cm$^2$/s) | Hydrodynamic diameter, $d_H$ (nm) |
|---|---|---|
| rat IgG | 63.2 ± 1.4 (38) | 10.39 ± 0.23 |
| rat IgG with 0.27 M mannitol | 68.9 ± 1.4 (7) | 9.53 ± 0.20 |
| rat IgG with 0.75 M mannitol | 68.4 ± 3.9 (8) | 9.61 ± 0.54 | mean ± SE (*n* measurements; *N* animals)

OSMOTIC ENHANCEMENT OF DRUG/THERAPEUTIC DELIVERY TO THE BRAIN FOLLOWING INFUSION OR INJECTION INTO THE CEREBROSPINAL FLUID

CROSS-REFERENCE TO RELATED APPLICATIONS

This application claims priority to U.S. provisional application 62/241,998, filed on Oct. 15, 2015, which is incorporated by reference herein and relied on in its entirety.

STATEMENT REGARDING FEDERALLY SPONSORED RESEARCH

This invention was made with government support under UL1TR0000427 and KL2TR000428 awarded by the National Institutes of Health. The government has certain rights in the invention.

BACKGROUND OF THE INVENTION

Delivering proteins and gene therapy vectors to widespread central nervous system (CNS) areas has to date been complicated by the barriers that exist between the bloodstream and the brain and spinal cord (Hammarlund-Udenaes et al. 2014). By "widespread," we mean that the drug or pharmaceutical is delivered throughout the brain and spinal cord and achieves more global delivery to the CNS.

Many of the primary central sites of administration that bypass these barriers remain viable options in clinical trials because they offer the potential of targeted CNS drug delivery and yield high brain and CSF levels with low systemic exposure. Delivering drugs into the cerebrospinal fluid (CSF) in the hope that they may be efficiently transported into adjacent brain and spinal cord tissue has long been among the most promising of these approaches because of its clinical practicability compared to more invasive intraparenchymal injections or direct brain infusion (convection-enhanced delivery) (Calias et al. 2014).

The relevant anatomy and specific compartments containing the CSF are shown in FIG. 1 and have been described extensively (Thorne. 2014; Dayson & Segal. 1996). Briefly, the brain and spinal cord are immersed in CSF, which helps to suspend the brain and avoid its distortion due to a buoyancy force that balances the downward force due to gravity (Thorne. 2014). The CNS and CSF are together encased within the meninges (the dura mater, arachnoid and the pia mater) which provide additional stability; the dura mater is anchored to the skull while the arachnoid, which forms the leptomeninges with the pia, is adherent to the dura mater. Leptomeningeal arteries and veins run within the subarachnoid space surrounded by CSF. The CSF occupies several cavities or chambers within the brain (the ventricular system) as well as a larger volume filling the subarachnoid space that surrounds the brain and spinal cord.

The human brain contains four ventricles (FIG. 1A-D): two large, c-shaped lateral ventricles, a single third ventricle between the thalamus and hypothalamus of each hemisphere, and a single tent-shaped fourth ventricle located between the cerebellum, pons and medulla. CSF is actively secreted by the choroid plexuses of the lateral, third and fourth ventricles (FIG. 1C) such that there is a brisk flow of CSF within the system. CSF flows from the lateral ventricles to the third ventricle via two interventricular foramina, then from the third ventricle to the fourth ventricle via the cerebral aqueduct, and, finally, exits into several cisterns and the subarachnoid space via three apertures, one located medially and two located laterally in the fourth ventricle (FIG. 1D). CSF is ultimately reabsorbed back into the blood supply through arachnoid projections into the venous sinuses and also along cranial and spinal nerve roots to extracranial lymphatics. Additional CSF outflow may also occur along the perivascular sheaths of major blood vessels. In adult human beings, roughly 15% of the total CSF volume is present within the ventricular system, with the remainder located within the fluid-filled cisterns and subarachnoid spaces outside of the brain and spinal cord.

There are three principal sites of infusion into the CSF compartments that are typically used: intracerebroventricular (into one or both of the brain's lateral ventricles or into the third or fourth ventricle), cisternal intrathecal (into the cisterna magna fluid space located beneath the cerebellum), and lumbar intrathecal (into the lumbar subarachnoid fluid space located below the conus medullaris termination of the spinal cord) (FIG. 2) (Thorne & Frey. 2001). ICV administration provides a strategy that can potentially deliver a variety of agents to wide areas of the CNS due to the circulation of CSF within the ventricular and extraventricular compartments. Similarly, intrathecal administration approaches also may potentially deliver drugs to widespread areas of the CNS; although anatomically the intrathecal routes accomplish somewhat less contact with the interior surfaces of the brain (i.e. the brain-ventricle interfaces) than with the intracerebroventricular routes, the intrathecal routes are less invasive and will not result in damage to parenchymal tissue if cannula placement and drug administration are performed properly However, decades of work have suggested that a severe diffusion limitation limits the transport of many macromolecules to only the most superficial regions of the brain and spinal cord when administered into the CSF (reviewed in Wolak & Thorne. 2013). Indeed, the resulting concentration gradients across the brain-CSF interface from diffusion are so steep that the levels of an infused 150 kDa antibody are expected to drop many million-fold just a few millimeters deep into the brain (See FIG. 3) (Wolak et al. 2015).

Needed in the art of drug delivery is an improved method of delivery to the CNS.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1A:
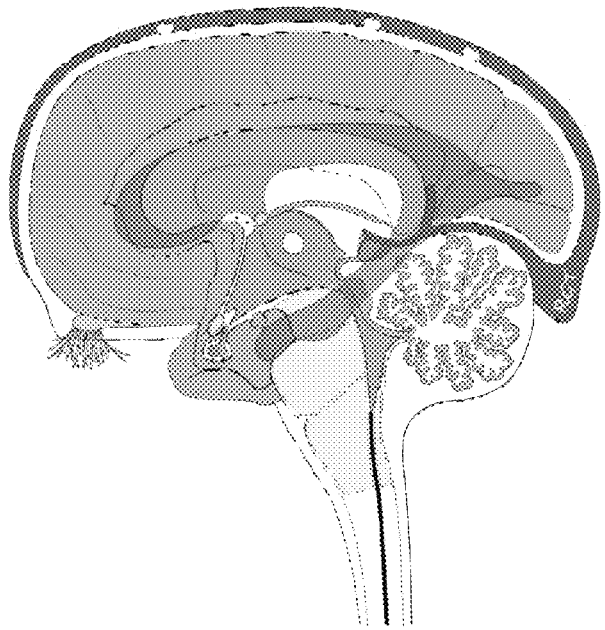
FIG. 1 (A-D). The ventricles in the brain interior are the prominent site of cerebrospinal fluid production, which flows from the ventricles outward to fill the subarachnoid space surrounding the brain and spinal cord. The human ventricular system viewed from (A) the midsagittal or (B) inferior brain surfaces. (C) A schematic of the human ventricles and the cerebrospinal fluid flow pattern (D). Cerebrospinal fluid is predominantly produced in the choroid plexus of the lateral, third, and fourth ventricles, flowing through the ventricular system (from lateral ventricles, through the interventricular foramina, into the third ventricle, through the cerebral aqueduct, and into the fourth ventricle) and out into the subarachnoid space surrounding the brain and spinal cord via the foramina of Luschka and Magendie.
Figure 1B:
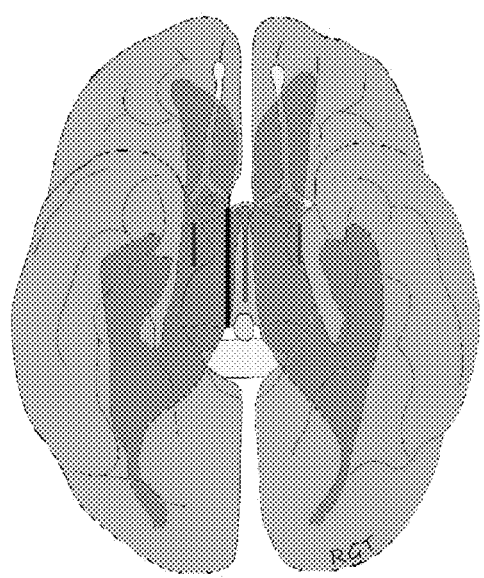
Figure 1C:
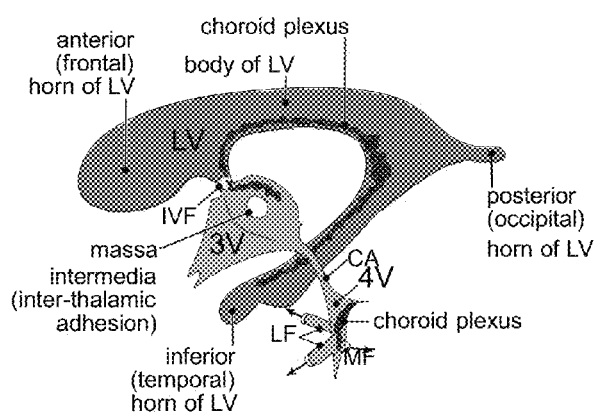
Figure 1D:
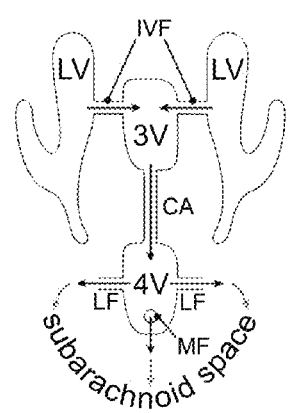
Figure 2:
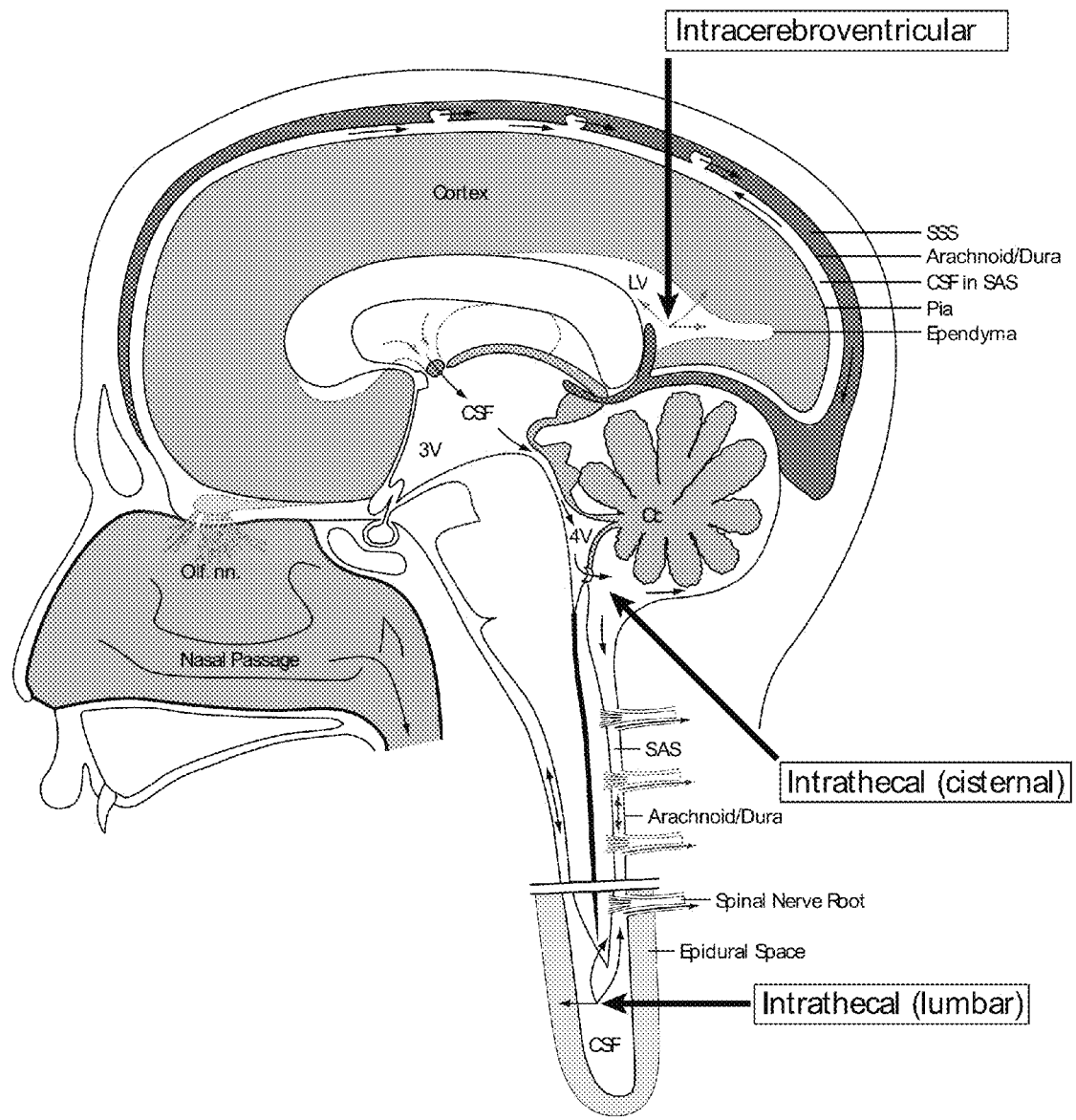
FIG. 2. Most common routes of administration into the cerebrospinal fluid include intracerebroventricular (into the brain ventricles) or intrathecal (cisternal) and intrathecal (lumbar) into the subarachnoid space. The most common routes of administration into the cerebrospinal fluid (large black arrows) include intracerebroventricular (administration into the ventricles in the brain's interior), or intrathecal, which may be performed into a subarachnoid cistern (most commonly the cisterna magna), or into the lumbar subarachnoid space surrounding the spinal nerves. Small gray arrows in the ventricular and subarachnoid spaces indicate direction of flow of the cerebrospinal fluid and small black arrows indicate drainage routes of cerebrospinal fluid into the blood of the dural sinuses (via arachnoid granulations) or along cranial or spinal nerves to lymphatics.
Figure 3A:
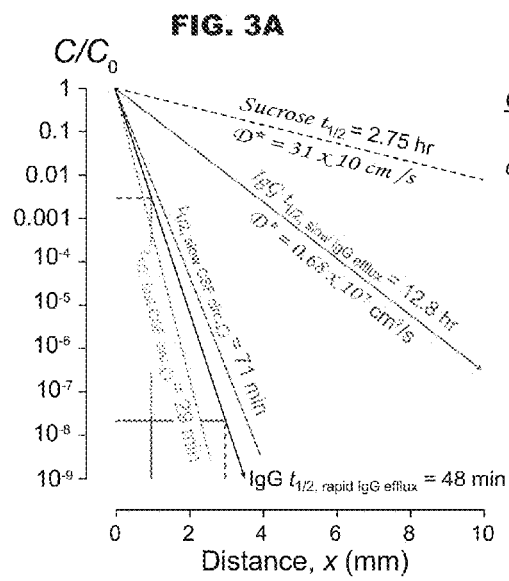
FIG. 3 (A-B). One potential mechanism of transport for molecules in the cerebrospinal fluid to enter the brain tissue is via diffusion into the brain tissue, but diffusion is slow and does not scale with larger brain size. (A) Concentration profiles modeling penetration from the CSF into adjacent brain for IgG and a small molecule (sucrose, 342 Da), based on in vivo diffusion and brain elimination data in the rat. (B) IgG concentration profiles with distance from the brain surface, predicted from diffusive transport from the CSF in brains of different size. Note the steep diffusion gradients do not scale with brain size (i.e. they will be the same in mouse and monkey as well as in human beings), greatly limiting distribution in the absence of PVS transport. (Wolak et al. 2015).
Figure 3B:
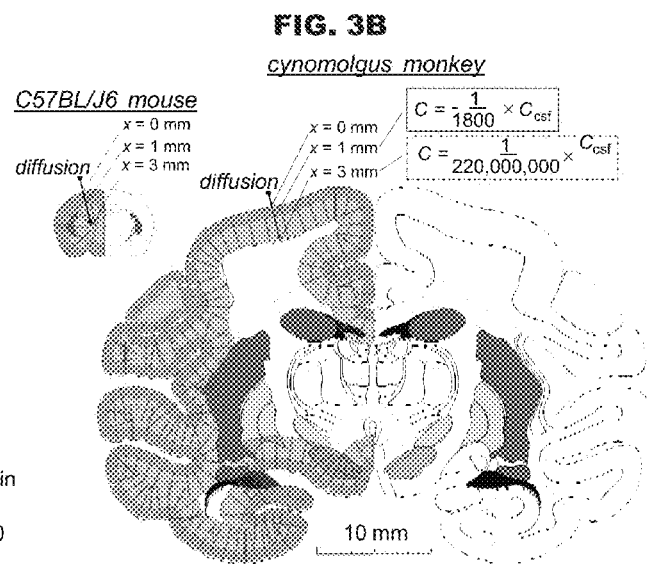

In one aspect, the present invention provides a method of enhancing therapeutic/drug transport to the perivascular space of the brain of a patient. The method includes introducing a therapeutic/drug and an osmolyte into a patient's cerebrospinal fluid (CSF), wherein the osmolyte can be introduced to the CSF at a concentration between 0.5 M and 12.9 M (dependent on the solubility upper limit of the osmolyte), and wherein the therapeutic/drug delivery to the perivascular spaces of cerebral blood vessels and parenchyma of the central nervous system is facilitated by the presence of the osmolyte.

In various versions of the invention, the osmolyte can be introduced to the CSF at an osmolality between 600 mOsm/kg and 13 Osm/kg. The osmolyte can be introduced to the CSF by way of injection or infusion. In preferred embodiments, the osmolyte can be introduced by intracerebroventricular injection or infusion, intrathecal intracisternal injection or infusion, or intrathecal lumbar injection or infusion. The introduction of the osmolyte can be simultaneous with the therapeutic/drug, or the osmolyte can be introduced into the CSF before the therapeutic/drug.

In certain embodiments, the therapeutic/drug can be a macromolecule or biopharmaceutical with a Stokes-Einstein hydrodynamic diameter in the range of 1 to 15 nm, 15 to 300 nm, 15 to 800 nm, or 10,000 to 30,000 nm. In some non-limiting examples, the therapeutic/drug can be a macromolecule or biopharmaceutical selected from the group consisting of a peptide, protein, antibody, RNA, asRNA, siRNA, DNA, cDNA, and viral vector. In other embodiments, the therapeutic/drug can be a stem cell. Various aspects of the invention may be used to treat central nervous system diseases such as lysosomal storage disorders, primary and metastatic brain cancer, neurodegenerative disorders, stroke, multiple sclerosis, CNS infections, and traumatic injury of the brain or spinal cord. The invention may also be used to treat neurodegenerative disorders such as Alzheimer's, Parkinson's, Huntington's, amylotropic lateral sclerosis, and prion diseases.

In another aspect, the invention provides a method of enhancing therapeutic/drug transport to the perivascular space of the brain of a patient. The method includes introducing a therapeutic/drug and an osmolyte into a patient's cerebrospinal fluid (CSF), wherein the osmolyte can be selected from either mannitol or sorbitol. The osmolyte can be introduced to the CSF at an osmolality between 850 mOsm/kg and 4,200 mOsm/kg to facilitate the delivery of the therapeutic/drug to the perivascular spaces of cerebral blood vessels and parenchyma of the central nervous system. In other embodiments, mannitol or sorbitol can be introduced to the CSF at a concentration between 0.5 and 1M. Additionally, mannitol or sorbitol may be introduced to the CSF at an osmolality between 850 mOsm/kg and 2100 mOsm/kg.

DETAILED DESCRIPTION OF THE INVENTION

The present invention has been described in terms of one or more preferred embodiments, and it should be appreciated that many equivalents, alternatives, variations, and modifications, aside from those expressly stated, are possible and within the scope of the invention.

Figure 4:
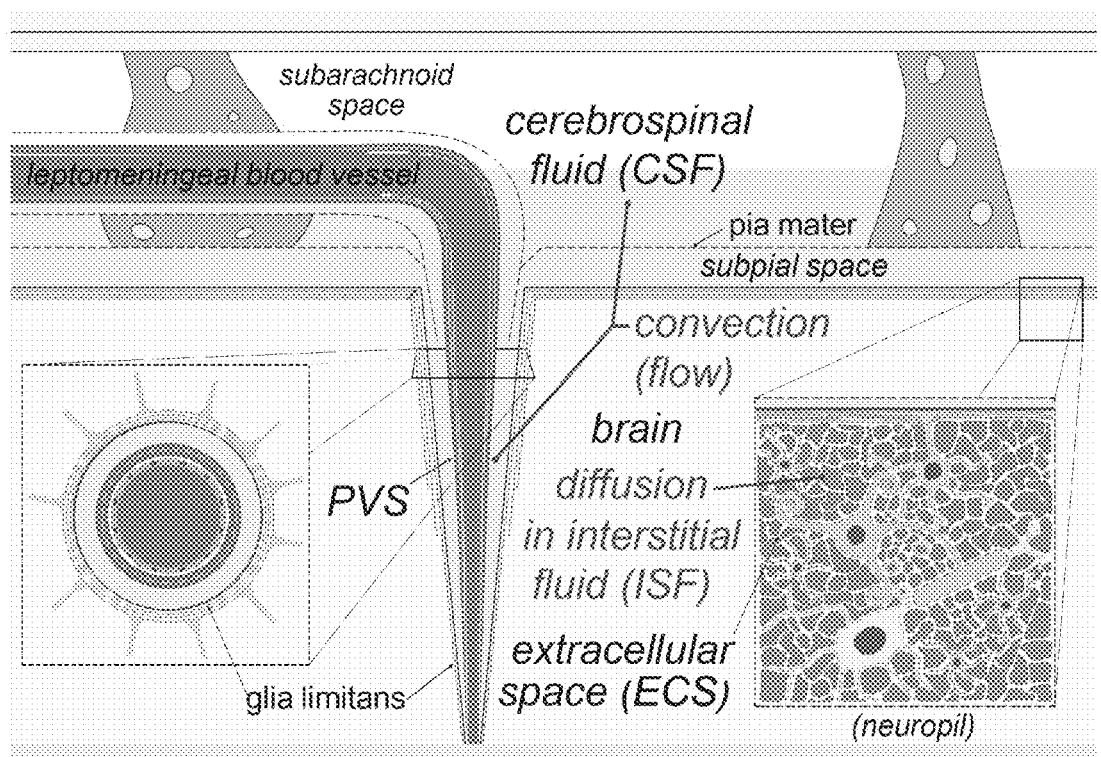
FIG. 4. One potential mechanism of transport for molecules in the cerebrospinal fluid to enter the brain tissue includes convective transport along perivascular spaces, which if accessed may provide substantial brain delivery. While evidence suggests diffusion will functionally limit extracellular transport of biologics to short distances (a few mms) in the brain parenchyma (neuropil), distribution within the CSF occurs over much greater distances by convection in the subarachnoid and ventricular spaces. Flow in the perivascular space (PVS) of penetrating blood vessels may allow further transport deep into the brain over greater distances than with diffusion, but only if biologics can access the PVS (Pizzo & Thorne. Unpublished; Wolak & Thorne. 2013).

There has long been a need for new methods and/or technologies that might improve upon the limited brain surface delivery of drugs from the CSF compartment. Recent work from our group and others (Wolak et al. 2015; Iliff et al. 2012 & 2013) have suggested that CSF-infused proteins may be delivered more completely to much deeper brain and spinal cord areas if they are capable of accessing and traveling by convection (flow) within perivascular spaces of cerebral blood vessels (FIG. 4). The perivascular space is a fluid-filled compartment surrounding CNS blood vessels that is bounded externally by arachnoid/pial cells in the subarachnoid space or the processes of astrocytes in the brain parenchyma. Importantly, a number of studies have suggested that the perivascular space has a substantial flow of fluid within it that is likely driven by pulsations associated with the cardiac cycle (Thorne & Frey. 2001; Lochhead et al. 2015; Wolak et al. 2015; Iliff et al. 2012 & 2013); flow is thought to occur in a defined direction, arteries→arterioles-→microvessels→venules→veins, such that a possible circulation of fluid has been hypothesized from superficial to deep locations of brain tissue (Iliff et al. 2012 & 2013). Research has also suggested that substances flowing into the brain along the perivascular spaces may further diffuse or flow into the parenchymal brain tissue surrounding the blood vessels potentially at points all along the pathway.

Because a perivascular space is a part of the structure of blood vessels in the brain and spinal cord all along the vascular tree supplying the full CNS tissue volume (from arteries to arterioles to microvessels to venules and then to veins), the space is a potential pathway for drugs and other substances to distribute from the cerebrospinal fluid in the subarachnoid space to all CNS target sites provided a drug or other substance can access them. In other words, these perivascular spaces could potentially allow for much more efficient and widespread delivery than diffusion across the brain-cerebrospinal fluid interface alone could ever produce.

The present invention concerns an osmotic approach for enhancing the access of infused macromolecules to these perivascular spaces and thereby achieving much more widespread CNS transport following delivery via, preferably, intracerebroventricular injection or infusion, intrathecal intracisternal injection or infusion, or intrathecal lumbar injection or infusion. This strategy could be paired with any existing or future approach where a drug is injected or infused into the CSF, i.e. either intracerebroventricular or intrathecal administration, and a more widespread distribution within the brain and spinal cord is needed. The strategy could potentially enhance the CNS delivery of any biologic or other large hydrophilic therapeutic substance (e.g. a peptide, protein, oligonucleotide such as siRNA or antisense, viral gene therapy vector, or nanoparticle as well as smaller hydrophilic drugs (e.g. products of chemical synthesis).

Indeed, there are a number of clinical trials that are beginning or ongoing that involve the administration of a variety of therapeutics into the CSF (see clinicaltrials.gov), and it is highly likely that many of these therapeutics would greatly benefit from enhanced perivascular access which would result in increased brain delivery. Clinical trials exist for CSF-administration of peptides (e.g., intrathecal oxytocin for pain), proteins (e.g, enzymes for a variety of metabolic disorders such as lysosomal storage diseases; PDGF-B protein analog for Parkinson's disease), oligonucleotides (e.g., nusinersen for spinal muscular atrophy; IONIS-HT-TRx for Huntington's disease), gene therapy vectors (e.g., AAV9 for Batten disease), stem cells (e.g., stem cells for autism spectrum disorder, amyotrophic lateral sclerosis, spinal cord injury, cerebral palsy, and multiple sclerosis), nanoparticles (e.g., liposome-encapsulated chemotherapeutics for brain cancers), and most relevant to the examples, antibody-based therapeutics (e.g., Rituximab for multiple sclerosis, antibody drug conjugates (particularly radio- or immunotoxin-immunotherapy) for brain cancers and CNS lymphomas), and antibody fragments like F(ab')2 for metastatic brain cancer).

Additionally, many clinical trials administer small-molecule drugs to the CNS, e.g., opioids for pain management, antibiotics for CNS infections, and chemotherapeutics for brain cancers. There are also many promising drugs for the treatment of neurological disorders that are currently being administered via other routes (e.g., intravenous administration) that may be administered in the future via the intrathecal or intracerebroventricular routes, that could also benefit greatly by osmotically enhanced perivascular access, for example antibody immunotherapy for treatment of Alzheimer's or Parkinson's disease.

Figure 5:
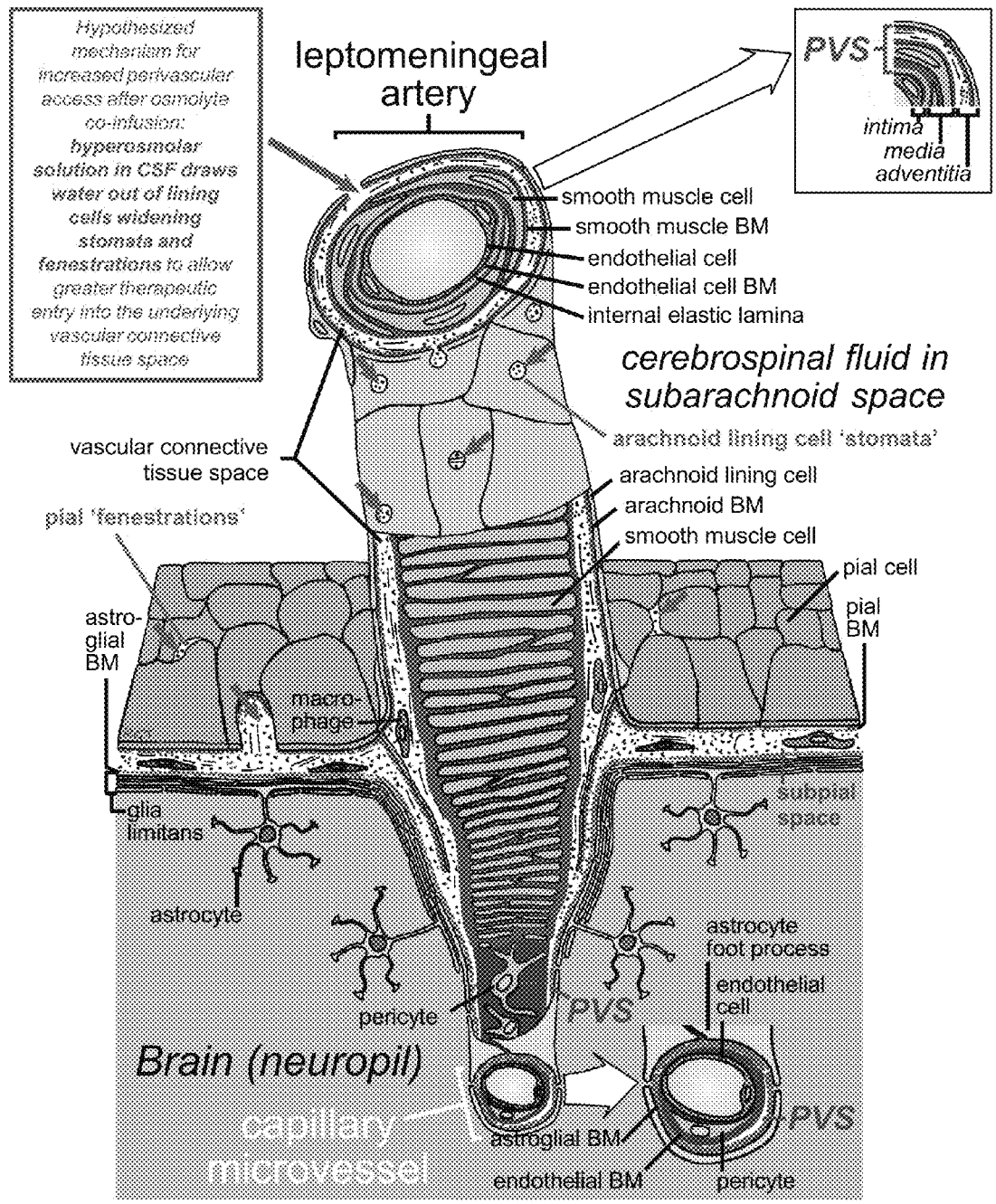
FIG. 5. New concept of perivascular space organization & potential sites of action for osmolytes infused into the cerebrospinal fluid. Access to the perivascular space from the cerebrospinal fluid is thought to occur via pores or openings in the pia mater and arachnoid lining cells, which ensheath blood vessels as they travel in the subarachnoid space. It is hypothesized that osmolytes administered into the CSF draw water out of the pial and arachnoid lining cells, causing them to shrink and the pores to widen, thus improving perivascular access to the molecules in the cerebrospinal fluid.
Figure 6:
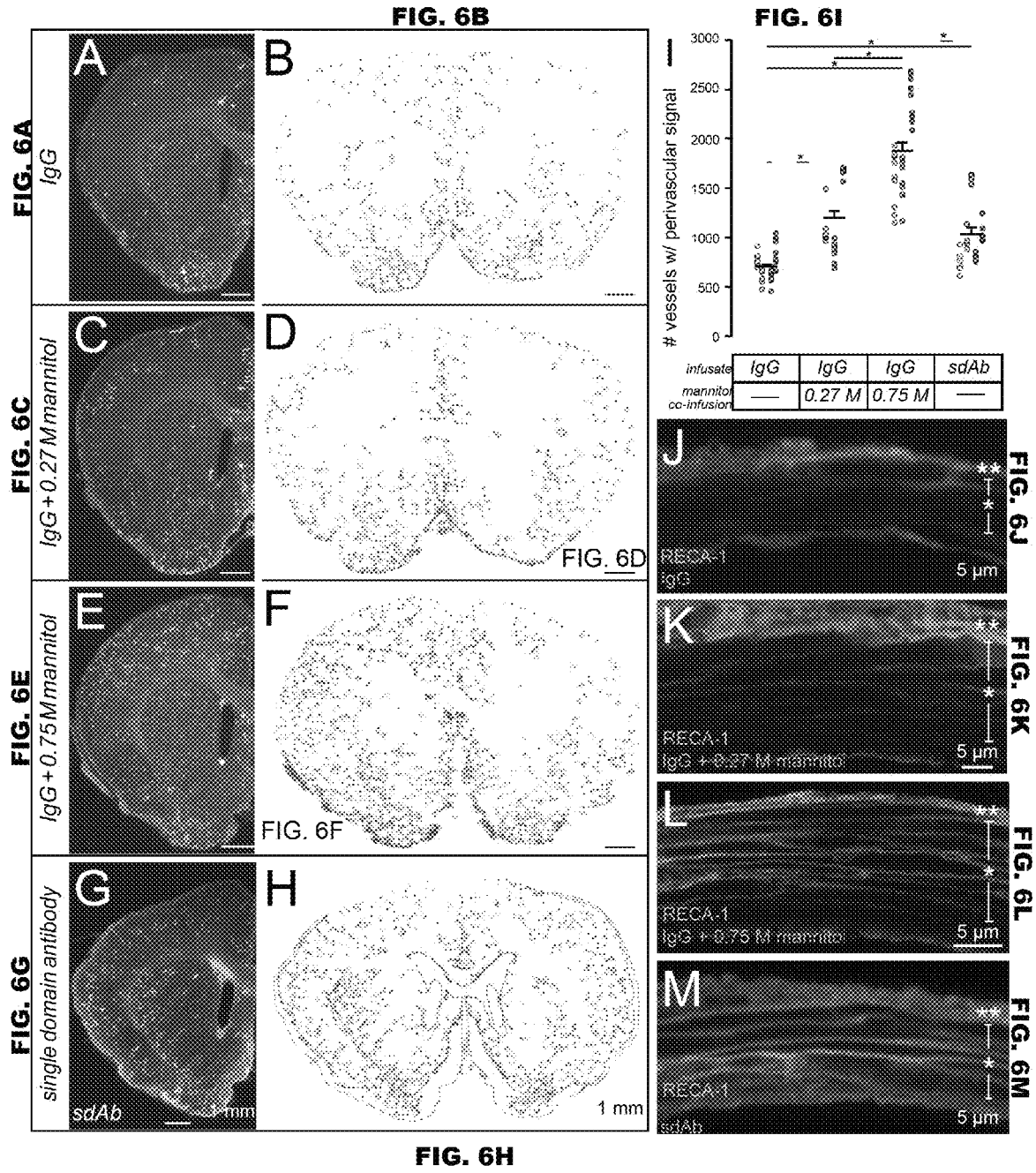
FIG. 6 (A-M). Mannitol co-infusion enhances full length 150 kDa antibody (immunoglobulin G, IgG) access to the perivascular space and smooth muscle BM in a dose-dependent manner. Representative images (A,C,E,G) and ImageJ counting (B,D,F,H) of perivascular IgG signal without mannitol co-infusion (A,B), IgG with 0.27 M mannitol co-infusion (C,D), IgG with 0.75 M mannitol co-infusion (E,F), or single domain antibody without mannitol (G,H). Co-infusion of IgG with 0.75 M mannitol (n=30, N=3) significantly increased the number of vessels accessed compared to 0.27 M mannitol co-infusion (n=24, N=3; p=0.0001) or IgG alone (n=27, N=4; p=1E-14; two-tailed t-test). Co-infusion of 0.27 M mannitol improved access compared to IgG as well (p=9E-7; two-tailed t-test). Infusion of the smaller ~15 kDa single domain antibody molecule (n=30, N=5) showed a significantly higher number of vessels accessed compared to IgG (p=4E-5), but single domain antibody showed no significant difference from IgG co-infused with 0.27 M mannitol (p=0.05; two-tailed t-test). Co-infusion of IgG with 0.75 M mannitol showed a significantly higher number of vessels had perivascular signal compared to the signal domain antibody (p=0.0009; two-tailed t-test), however the single domain antibody still shows greater surface penetration. Confocal imaging of the cerebral internal carotid artery (J-M) demonstrated IgG (J-K) or single domain antibody (M) signal in the putative vascular connective tissue space (**). For IgG with (K-L) or without (J) mannitol, however, access to the BM of the smooth muscle layer (*) is modestly increased for 0.27 M mannitol co-infusion (K), and strikingly increased for the 0.75 M mannitol co-infusion (L), with penetration of the smooth muscle layer similar to that of the smaller single domain antibody (M).

Without being limited to a particular method, we conceive that such an osmotic approach works by pulling water out of arachnoid and/or pial cells that line the cerebral blood vessels and function as 'gatekeepers' to the perivascular space because they provide only limited sites of entry via stomata (pores/openings), fenestrations, and other gaps. Co-infusing an osmolyte, such as mannitol or sorbitol, makes more of these entry sites available to large macromolecules and also allow their distribution to be enhanced by facilitating better access to perivascular compartments such as the adventitia and the media (FIG. 5).

Therefore, by facilitating access to the perivascular space, our osmotic approach would allow a CSF-administered drug or therapeutic to be transported by flow (convection) within the perivascular spaces to a much greater volume of brain and spinal cord tissue than compared to if the drug were injected or infused alone. The potential of this approach is great given that there are currently multiple clinical trials in progress where protein therapeutics (e.g. large enzymes and antibodies) are being intrathecally infused for the treatment of lysosomal storage disorders and metastatic cancer to the brain (Calias et al. 2014). Widespread delivery with CSF infusions may also be a promising approach for Alzheimer's or Parkinson's disease immunotherapies using antibodies.

In one general embodiment, the present invention is a method of enhancing drug/therapeutic transport to and within the perivascular space of the brain of a patient, preferably a human patient, comprising the step of introducing a drug/therapeutic and an osmolyte of the present invention, either together or separately, into the patient's central nervous system, wherein the osmolyte is at a preferred concentration of between 0.4 and 2.0 M or at an osmolality of 650 mOsm/kg to 2100 mOsm/kg during introduction.

In a preferred embodiment, the introduction is by way of injection or infusion, preferably intracerebroventricular injection or infusion, intrathecal intracisternal injection or infusion, or intrathecal lumbar injection or infusion.

In a preferred version of the present invention, the osmolyte is either mannitol or sorbitol. However, other osmolytes include those described below.

In a preferred version of the present invention, the combination of drug/therapeutic and osmolyte is in a volume of between 1 and 60 ml per hour and results in a final molarity of the osmolyte within the patient's cerebral spinal fluid greater than 0.086 M.

In general, the method of the present invention could enhance the CNS delivery of any biologic or other large hydrophilic therapeutic substance (e.g. a peptide, protein, oligonucleotide such as siRNA or antisense, viral gene therapy vector, nanoparticle, or stem cells). Preferable therapeutic agents include biologics or therapeutic substances greater in size than 1 kDa because smaller agents may be expected to not experience appreciable hindrance to their access to the perivascular pathways.

Figure 9:
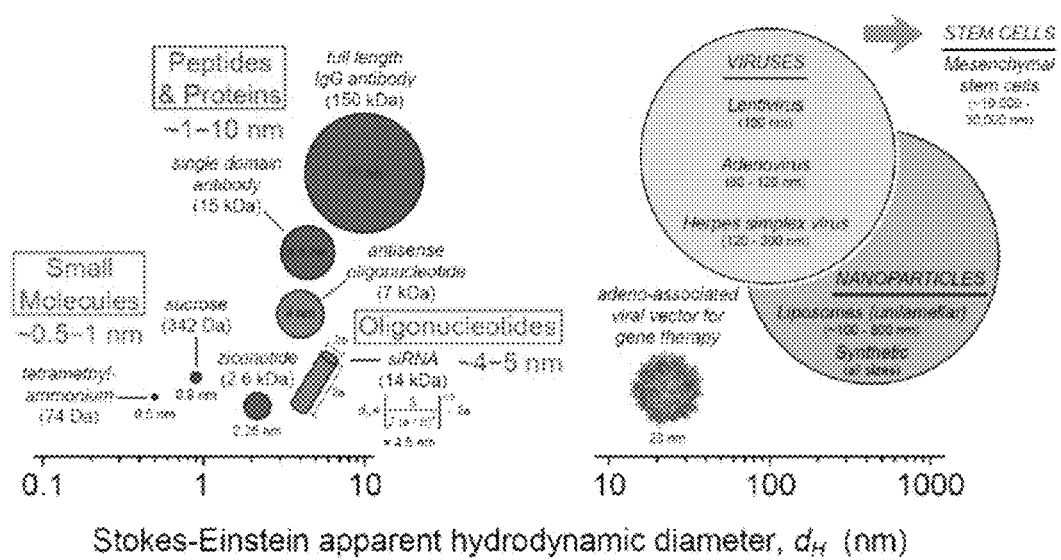
FIG. 9. Relative sizes of potential therapeutics: small molecules, peptides, proteins, oligonucleotides, viruses, nanoparticles, and cells. Values obtained mostly from diffusion measurements in free solution and subsequent transformation to apparent hydrodynamic diameters using the Stokes-Einstein equation (Thorne et al. Journal of Neurophysiology, 2004). Primary sources: Bloomfield et al. Nucleic Acids, 2000; Davidson & Breakefield. Nature Reviews Neuroscience, 2003; Ge et al. Stem Cell Reviews and Reports, 2014; Hoogduijn et al. BMJ, 2013; Nam et al. Journal of Virology, 2011; Torchilin. Nature Reviews Drug Discovery, 2005; Wolak & Thorne. Molecular Pharmaceutics, 2013. Additional unpublished data on antibodies, antisense oligonucleotides, siRNA, and adenoassociated viruses from Wolak, Wilken-Resman, & Thorne. Relative sizes rescaled from left to right panel.

Potential CNS therapeutics of the present invention can span several orders of magnitude in size, both in molecular weight and hydrodynamic size, as shown in FIG. 9. The hydrodynamic size of molecules depends on their ability to fold or compact themselves (due to steric effects) and the water shell that surrounds the molecule in solution (either the drug formulation or the CSF after administration). We envision this osmotic enhancement method can aid in entry to the perivascular spaces, especially for molecules greater than 1 kDa in molecular weight, or 1 nm in hydrodynamic diameter. The present invention is preferred for molecules greater than 1 nm in hydrodynamic diameter and especially preferred for molecules greater than ~3 nm in hydrodynamic diameter (the approximate diameter of a 5 kDa protein).

Examples of current macromolecule therapeutics and their approximate size include: peptide and protein drugs including oxytocin, zoconotide, lysosomal enzymes, and antibody-based therapeutics (1-150 kDa, 1-10 nm); oligonucleotides including siRNA and antisense oligonucleotides (5-15 kDa, 3-5 nm); gene therapy vectors including adeno-associated virus, lentivirus, adenovirus (20-300 nm); and stem cell therapies (10,000-30,000 nm). While small molecule drugs (smaller than approximately 1 kDa or 1 nm) administered into the CSF are likely to distribute further than macromolecule drugs by diffusion, it is possible (depending on the drug properties) that small molecule drugs could also benefit from increased perivascular access. However, it is likely that large molecule drugs (greater than 1 nm in hydrodynamic diameter) would benefit the most from increased perivascular access, as their distribution is otherwise too limited to be therapeutically relevant. (Thorne, 2004) The present invention is especially useful for molecules greater than 3 nm.

Examples

In General

As the figures disclose, we have shown that co-infusing 0.75 M mannitol with a labeled protein tracer, a fluorescently labeled 150 kDa full length immunoglobulin G (IgG) antibody, results in dramatically greater brain distribution via the perivascular spaces. We envision that a significant increase in drug access to the perivascular spaces will be optimal for enhancing brain distribution to achieve more widespread delivery to most central nervous system target sites (e.g. as revealed by quantitative counting of cerebral blood vessel profiles with fluorescent signal emanating from a tracer molecule infused into the CSF)—Our preliminary data indicates for a molecule such as an immunoglobulin G antibody, a greater than 1.7-fold increase in perivascular space access, or preferably greater than a 2-fold increase in perivascular space access, will be optimal. We propose that co-infusion of a drug of interest with mannitol, sorbitol and other such non-toxic osmolytes at concentrations above 5% (0.27 M in the case of sorbitol/mannitol) or with an osmolality greater than 600 mOsm/kg, preferably between 0.4 M and 12.9 M (dependent upon the aqueous solubility limit of the osmolyte) and most preferably between 0.5 and 2 M, may provide a new strategy to greatly enhance the effectiveness of injection/infusion of biologics such as antibodies, enzymes and gene therapy vectors.

Intrathecal infusions of hypertonic mannitol solutions are well tolerated in animals (Speck et al. 1988). 5% (0.27 M) sorbitol (an isomer of mannitol and a glucose metabolite) has been routinely used for cisternal infusions of AAV gene therapy vectors, e.g. in non-human primates (Gray et al. 2013; Samaranch et al. 2013). Use of sorbitol at this lower concentration has been employed to stabilize the AAV vectors. There has not been any suggestion that we know of in the published literature that this use of sorbitol could enhance vector distribution. Key to the present invention is that to date the effects and mechanisms of co-infused osmolytes on intrathecal drug delivery have not been defined and no data yet exists to our knowledge on the ability of such an approach to facilitate access to the perivascular space for widespread brain delivery.

We hypothesized that intrathecal mannitol would osmotically draw water out of the lining cells of leptomeningeal blood vessels, smooth muscle cells of the media, and/or lining cells of the pia (FIG. 5), thereby opening intercellular gaps and widening smooth muscle BM extracellular spaces for enhanced perivascular space access and distribution. Indeed, ex vivo imaging in rats has shown that intracisternal infusions of Alexa fluor 488-labeled IgG in a 0.75 M mannitol solution had a profound effect, doubling the number of blood vessels with IgG PVS signal compared to IgG infused without mannitol when quantified using ImageJ particle analysis (FIGS. 6A, 6B, 6E, 6F & 6I).

Furthermore, mannitol co-infusion noticeably increased IgG access to the smooth muscle BM space, comparable to that seen with a much smaller single domain antibody fragment 1/10th the size of IgG (~15 kDa) (FIGS. 6J-6M). We have recently demonstrated that mannitol also improves perivascular and smooth muscle basement membrane access in a dose-dependent manner (FIGS. 6C-F, 6I, & 6J-6L. Our experiments, reported below and in the figures, show that co-infusion of 0.75 M mannitol resulted in a 2.5-fold increase in the number of perivascular spaces accessed by IgG alone, and a 1.5-fold increase compared to co-infusion of 0.27 M mannitol with IgG (FIG. 6I). Co-infusion of 0.27 M mannitol resulted in a 1.7-fold increase over IgG alone. Additionally, IgG co-infused with 0.75 M mannitol markedly improved IgG access to the basement membrane of the smooth muscle layer, while 0.27 M mannitol co-infusion resulted in no visible improvement (FIG. 6J-6L).

Materials and Methods for the Experiments Disclosed in FIGS. 1-9

Intracisternal Infusions

Female Sprague-Dawley rats (180-240 g) were anesthetized to a surgical plane of anesthesia using 1.3 g/kg intraperitoneal urethane (boostered to effect), tracheotomized, and placed in a stereotaxic frame (Stoelting). Atropine (0.1 mg/kg every two hours) was given subcutaneously to reduce fluid secretion in lungs. An incision was made on the back of the neck and the muscles were dissected from the occipital bone to expose the atlanto-occipital membrane, which was retracted to reveal the dura overlying the cisterna magna. A custom cannula (~1 cm long) made of 33 GA polyether ether ketone (PEEK, Plastics One) was connected to a Hamilton syringe controlled by an infusion pump (Quintessential Stereotaxic Injector, Stoelting) via polyethylene-10 tubing (Solomon Scientific). The tubing was pre-filled with infusate (i.e., antibody solution with or without mannitol), the dura punctured with a dental needle, and the PEEK cannula immediately inserted at a 60-degree angle from the horizontal, advanced 1 mm into the cisterna magna, and sealed with cyanoacrylate.

For ex vivo fluorescence, AlexaFluor488 goat-anti-rabbit IgG in PBS (as provided) or in PBS with mannitol (described below) was infused at 1.6 uL/min for 50 minutes (80 uL total), a rate that is expected to be physiological as it is approximately half the CSF production rate and has been shown not to increase intracranial pressure in rats (Yang et al. J Trans Med 2013). The abdominal aorta was then cannulated and thirty minutes after the infusion completed the animal was perfused with ~50 mL ice cold 0.01 M PBS followed by ~450 mL 4% paraformaldehyde in 0.1 M phosphate buffer following a blood draw. The brain was removed and placed in 4% paraformaldehyde or phosphate buffered saline overnight, then sliced into 100 micrometer sections using a vibratome. Sections were imaged on an Olympus MVX10 using an Orca-flash 2.8 CMOS camera (Hamamatsu), a Lumen Dynamics X-Cite 120Q illuminator and an appropriate filter set (Chroma, U-M49002XL).

In some animals, 30 minutes after IgG infusion 0.5 mL blood was drawn via cardiac puncture or abdominal aorta cannula and kept on ice. Blood was spun for 10 minutes at 3,000 g and the supernatant then spun for 10 minutes at 10,000 g. The supernatant was removed for fluorescence quantification on a microplate reader (FLUOstar Omega, BMG LABTECH) and IgG concentration determined by comparison with a standard curve.

Immunohistochemistry and Confocal Microscopy

After slicing, free floating sections were washed three times in 0.01 M PBS for 5 minutes, blocked with 3% goat serum for one hour at room temperature, incubated in 3% goat serum with mouse-anti-rat endothelial cell antigen 1 (RECA-1) primary antibody (Abcam ab9774; 1:1000 dilution) overnight at 4 C. The following day sections were washed in PBS, incubated with goat-anti-mouse AlexaFluor405 (Life Technologies A-31553; 1:500 dilution) for one hour at room temperature, washed in PBS, and mounted on slides using Prolong Gold Antifade (Life Technologies). Sections were imaged on an Olympus FV1000 confocal microscope using FLUOVIEW software.

Mannitol Co-Infusion

AlexaFluor 488 goat-anti-rabbit IgG was prepared in 0.27 M or 0.75 M mannitol in 0.01M PBS using 0.5 mL Amicon Ultra 100 kDa molecular weight cutoff centrifugal filters for buffer exchange. IgG was added to the filter and washed/spun from 0.5 mL three times with 0.27 M or 0.75 M mannitol solution (osmolality 507 mOsm/kg and 988 mOsm/kg, respectively); each spin was 10 minutes at 14,000 g. Recovery spin was 2 minutes at 1,000 g. Concentration of IgG protein (absorbance at 280 nm) was measured using a NanoDrop 2000 (Thermo Fisher), and after concentration/buffer exchange in mannitol the protein concentration was diluted to the same concentration so animals received identical amounts of IgG whether administered in provided buffer or buffer with mannitol.

Perivascular Counting

To quantify perivascular signal between treatments, images were opened in ImageJ/Fiji, thresholded to eliminate background, and the Analyze Particles command was used to count and outline 'particles', or perivascular signal, with no restrictions on size or circularity, as well as providing additional information such as circularity, area, and average size. The command also outputs numbered outlines (in red) of the counted perivascular signal shown in FIGS. 6B, D, F, and H.

Summary/Conclusions for the Experiments Disclosed at FIGS. 1-9

0.75 M mannitol enhanced brain distribution by greater than 50% compared to the published sorbitol concentration (0.27 M) that has been employed as a stabilizer, not for delivery enhancement. Infusing mannitol, sorbitol, or other such osmolyte at an osmolality above 600 mOsm/kg but ideally at a concentration of at least 0.5M and preferably around 0.75 M represents a novel CNS delivery enhancement method for CSF input. This new approach could benefit existing clinical trials to enhance the delivery of enzymes to sick children with neurotropic lysosomal storage disorders as well as current trials where an antibody such as trastuzumab is delivered to the brain in patients with brain metastases from breast cancer. Furthermore, this approach could benefit the delivery of the antisense oligonucleotide nusinersen in children with spinal muscular atrophy, AAV9 for Batten disease, and stem cells for brain and spinal cord injury. The present invention could offer better immunotherapy approaches for metastatic lung cancer or melanoma to the brain, where antibody access and distribution have historically been challenging. Finally, enhanced antibody delivery to the brain in Alzheimer's and Parkinson's patients may yield better efficacy as a potentially new central immunotherapy approach.

Therapeutic Indications of the Present Invention

Many applications have been envisioned for cerebrospinal injections or infusions of drugs. The intrathecal and/or intraventricular routes have been clinically utilized, mostly experimentally to date, to accomplish central nervous system delivery of enzymes for lysosomal storage diseases, antibodies for brain cancers, antibodies for stroke, growth factors for Parkinson's disease and Alzheimer's disease, and many others (Calias et al. 2014; Thorne & Frey. 2001). The lone example of a FDA-approved biologic that acts in the brain is intrathecal infusion (lumbar) of ziconotide, a 2.6 kDa peptide drug. Intrathecal administration of antibodies for the treatment of breast cancer brain metastases has been appreciated to offer much higher CSF drug concentrations at smaller doses and with less toxicity than systemic (intravenous) antibody infusions (Park et al. 2015).

The full list of potential indications of the method of the present invention might reasonably include just about any central nervous system disease or disorder—diseases such as metabolic and lysosomal storage disorders, primary and metastatic brain cancer, neurodegenerative disorders, stroke, multiple sclerosis, CNS infections, psychiatric disorders and traumatic injury of the brain or spinal cord. Lysosomal storage disorders may include mucopolysaccharidoses, mucolipidosis, and others. Neurodegenerative disorders may include Alzheimer's, Parkinson's, Huntington's, amylotropic lateral sclerosis, spinal muscular atrophy, cerebral palsy, and prion diseases. Infections of the central nervous system where an active drug must be delivered to and access widespread central nervous system areas would also potentially benefit from the scope of the present invention (Cook et al. 2009).

Preferred macromolecule therapeutics of the present disclosure include molecules with a Stokes-Einstein hydrodynamic diameter between 1-10 nm such as peptides, protein drugs, lysosomal enzymes, and antibody-based therapeutics; molecules between 3-5 nm such as siRNA and antisense oligonucleotides; macromolecular assemblies between 20-300 nm such as gene therapy vectors; and macromolecular assemblies between 10,000-30,000 nm such as stem cell therapies.

In summary, in a preferred version of the invention, the therapeutic/drug is selected from a group consisting of those with a Stokes-Einstein hydrodynamic diameter of 1-10, 10-30, 30-100, 100-800, 800-10,000, and 10,000-30,000 nm.

Other embodiments of the invention could include small molecule therapeutics, such as those smaller than 1 kDa or 1 nm that are administered into the CSF. It is possible that small molecule drugs could benefit from increased perivascular access depending on the properties of the drug.

Therapeutics/Drugs of the Present Invention

Active drugs (therapeutics) that would be envisioned to benefit from the proposed invention potentially include any therapeutic molecule, large macromolecule, or macromolecular assembly greater than approximately 1 kDa or 1 nm in size such as enzymes, antibodies, peptides, proteins, genetic material, and gene therapy vectors. Examples may include biopharmaceuticals, macromolecules, therapeutic agents, and others. Biopharmaceuticals may include antibodies, peptides, proteins, vectors for gene therapy (including viral and non-viral vectors), stem cells, and others. Macromolecules may include any oligonucleotide, such as RNA, asRNA, siRNA, DNA, and cDNA. Therapeutic agents may include any other chemicals, such as therapeutic small molecules and nanoparticles (i.e., liposomal, polymeric, dendrimers, solid nanoparticles, hydrogels, nanotubes, micelles, and nanocrystals) that would benefit from a greater distribution within the central nervous system during and following infusion into the cerebrospinal fluid. By "therapeutic" or "drug" we mean to include all manner of treatment pharmaceuticals including compositions that merely slow a disease or symptom or a composition that is of prophylactic benefit.

Preferred Osmolytes within the Scope of the Invention

Our existing data covers mannitol at two different concentrations and osmolalities. We speculate the same effect will occur with other organic osmolytes such as polyols/polyhydric alcohols (mannitol and sorbitol), sugars (e.g. sucrose or maltose), and other certain amino acids and their derivatives (glycine, proline). Preferred osmolytes of the present invention are mannitol and sorbitol.

Osmolyte Formulation and Dose Range

Mannitol (or any other osmolyte of the present invention) may be in a dry solid (powder) or liquid (usually aqueous solution in saline, buffer, artificial CSF) and may be combined with a dry solid (perhaps a lyophilized powder) or liquid therapeutic that likely has a variety of additional excipients for stability, preservation, etc. Mannitol may be combined with a therapeutic as a dry solid or as a solution (in water, saline, buffer, buffered saline, or artificial CSF with or without excipients/stabilizers/preservatives) at a concentration greater than 0.27 M.

If combined as a solid, the mannitol with therapeutic would then preferably be added to a liquid (water, saline, buffer, buffered saline, artificial CSF) prior to infusion. CSF infusions are envisioned to be in aqueous formulations.

Once the mannitol and therapeutic are prepared as a solution for infusion, it may be administered into the CSF, preferably by the routes including intracerebroventricular injection or infusion, intrathecal intracisternal injection or infusion, or intrathecal lumbar injection or infusion for a period of time and a flow rate most likely dictated by the therapeutic. In some cases it may be more desirable to pre-infuse a mannitol solution intrathecally so that it can act on the local environment before therapeutic is administered intrathecally, or in cases where the therapeutic may not be stable or has undesired interactions with mannitol.

Former studies have used mannitol, sorbitol, sucrose, and other organic osmolytes for purposes of drug stability and solubility. These are often low amounts as they are excipients to the formulation of active compound. For example, 5% sorbitol is often included in intrathecally applied viral vector formulations for improved stability. We have infused mannitol at concentrations of 0.27 M (5%) and 0.75 M (14%) and show a dose-dependent increase in perivascular access between 0.27 M and 0.75 M, though 0.27 M also results in a slight increase compared to controls. Thus a higher concentration of mannitol is likely to improve distribution of an intrathecally applied therapeutic, that is, 0.75 M mannitol would be more desirable. Thus, we envision the invention to include a concentration range of greater than 0.4 M to 2 M mannitol or sorbitol, the solubility limit of mannitol just above body temperature (40° C.), with a preferred range of 0.5 to 1 M.

Another way to define the osmolyte concentration of present invention is in terms of osmolality: A suitable organic osmolyte is one that is at an osmolality higher than that of 0.27 M mannitol in isotonic saline. We have measured the osmolality of both the 0.27 M mannitol (507-564 mOsm/kg) and 0.75 M mannitol (988-1126 mOsm/kg) solutions. A preferred osmolyte of the present invention has an osmolality above 570 mOsm/kg.

Solubility Details

Mannitol: at 40 C (just above body temperature)=1.90-1.94 M (Mullin, J W. *Crystallization*. Butterworth-Heinemann, 2001; Seidell, A. *Solubilities of inorganic and organic compounds c.* 2. D. Van Nostrand Company, 1919.) Merck Index references Creighton & Klauder. *J Franklin Inst.* 1923, which gives a similar value. At room temperature solubility is 1 M (Merck Index).

Sorbitol: Merck Index: freely soluble in water up to 83% which is 12.9 M;

Mannose: 4.22 M (Gabas et al. *J Chem Eng Data.* 1988.) at 25 C; 13.9 M (Merck Index)

Xylose: 8.32 M (Merck Index), 3.66 M (Gabas et al. *J Chem Eng Data.* 1988.) at 25 C Maltitol: 5.81 M at 37 C (body temperature)

Xylitol: 4.2 M (Merck Index)

Polyols include: mannitol, sorbitol, erythritol, isomalt, lactitol, maltitol, xylitol Glycine: 2.90 M (Needham et al. *J Pharm Sci.* 1971) at 25 C; 3.3 M at 25 C and 5.21 M at 50 C (Merck Index)

L-Alanine: 1.67 M (Needham et al. *J Pharm Sci.* 1971) at 25 C

L-Valine: 0.514 M (Needham et al. *J Pharm Sci.* 1971) at 25 C

L-Phenylalanine: 0.208 M (Needham et al. *J Pharm Sci.* 1971) at 25 C

Figure 7:
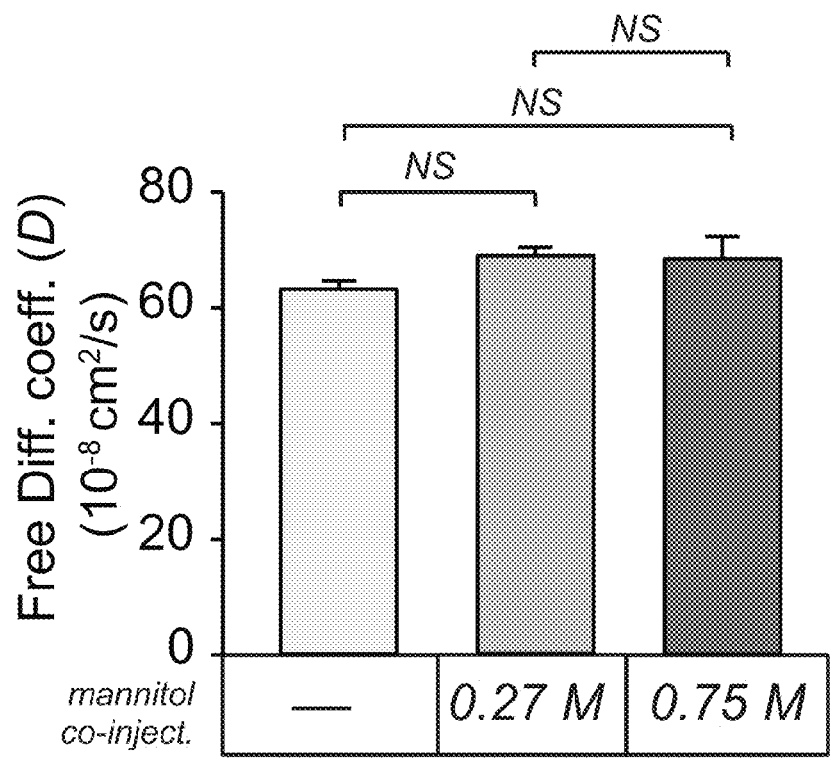
FIG. 7. Free diffusion coefficient of IgG is not significantly altered in the presence of mannitol, suggesting that IgG stability is not impacted. The diffusion of rat IgG was measured using integrative optical imaging (described in detail in Thorne & Nicholson. PNAS, 2006; Thorne et al. PNAS, 2008; & Wolak, Pizzo & Thorne. J Control Rel, 2015). Measurements were performed in dilute agarose gel for the free diffusion coefficient (D) without mannitol, or with 0.27 M or 0.75 M mannitol. The free diffusion of IgG is unaffected by mannitol.
Figure 8A:
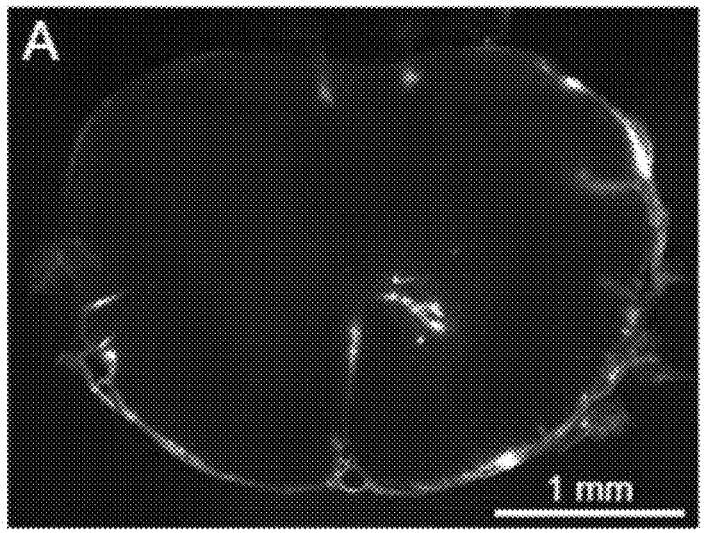
FIG. 8 (A-C). Fluorescence imaging of spinal cord slices shows mannitol increases perivascular access. The spinal cord has a simple structure—an outer spinal white matter that has few blood vessels and an inner spinal gray matter which has a dense network of blood vessels. (A) After intrathecal infusion of IgG without mannitol, only a few perivascular spaces in a slice of the upper cervical spinal cord contain IgG, and most of the IgG signal is in the highly-vascularized spinal gray matter. (B) After IgG with 0.27 M mannitol co-infusion, there appears to be a slight increase in the number of IgG perivascular profiles in the spinal gray compared to IgG alone. (C) After IgG with 0.75 M mannitol co-infusion, there is a striking increase in the number of perivascular spaces with IgG signal, particularly in the spinal gray matter.
Figure 8B:
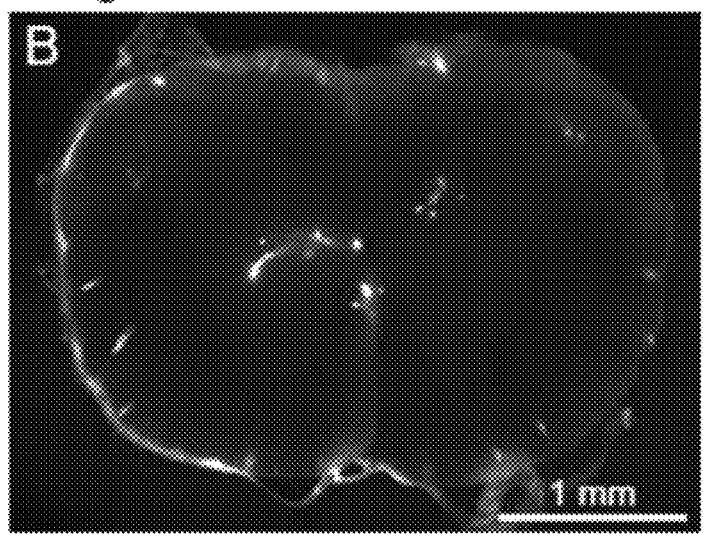
Figure 8C:
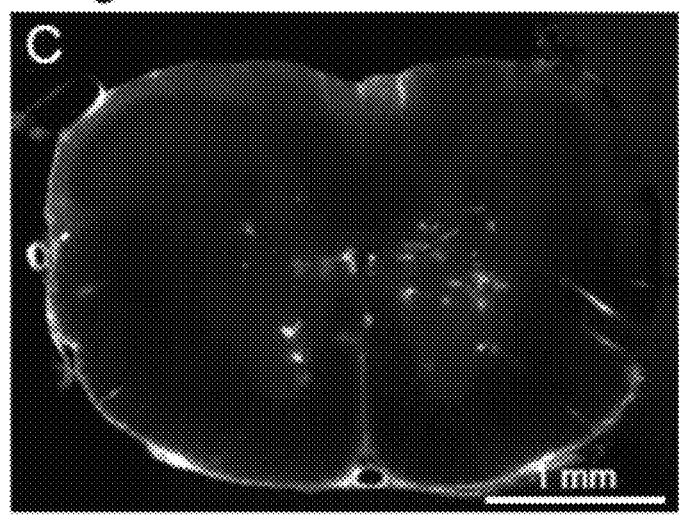

NOTE—Mannitol at the concentrations we have used within the Examples does not appear to have any effect on the structure of immunoglobulin G antibody (FIG. 7). The hydrodynamic diameter of IgG antibody, as determined from quantitative diffusion measurements and calculation of diameter from the diffusion coefficient using the Stokes-Einstein relationship, is unaffected by mannitol at 0.75 M. This differentiates the present invention from the typical purpose of osmolyte stabilizers, which is to stabilize the formulation and prevent aggregation, not to improve delivery.

Prophetic CSF Dose of Osmolyte Achieved

Mannitol administered at different concentrations and different volumes can achieve similar concentrations of mannitol in the CSF. In rats, we currently infuse either 80 microliters of 0.75 M mannitol into approximately 250 microliters of CSF resulting in a concentration of mannitol in the CSF of approximately 0.24 M, or 80 microliters of 0.27 M mannitol in 250 microliters of CSF resulting in a concentration of mannitol in the CSF of approximately 0.086 M (assuming all 80 microliters was administered instantaneously into the CSF and assuming it is instantly mixed throughout the entire CSF compartment). A suitable concentration of mannitol (or other osmolyte) within the CSF of a typical patient will be greater than 0.086 M, preferably between 0.086 and 1.0M. This concentration will be dependent on infusion rates. It may be possible to achieve a higher concentration of mannitol, for example, if one were to infuse for a long enough period of time at a fast flow rate.

Preferred Routes of Administration—Intracerebroventricular or Intrathecal

This invention involves the administration of mannitol or sorbitol (or other osmolyte) along with a therapeutic agent into the cerebrospinal fluid. The most common routes of administration into the cerebrospinal fluid (and the most typical for the present invention) include intracerebroventricular (ICV) and intrathecal (either into the lumbar subarachnoid space or cisternal subarachnoid space) (Thorne & Frey. 2001). Briefly, ICV administration is achieved by inserting a cannula through a hole in the skull, through the brain tissue, into a CSF-filled ventricle of the brain; a single cannula may be inserted (e.g. into either of the two lateral ventricles) or two cannulas may be inserted (into both lateral ventricles). The cannula may be connected to a syringe or infusion pump for one-time administration, or a controlled device, such as an Ommaya reservoir. Intrathecal intracisternal infusions are less frequently performed in humans due to the proximity of the cisterns to vital brain tissues. However, intrathecal infusion devices (e.g. Medtronic devices) can be inserted in the lumbar subarachnoid space and a catheter extended upwards toward the cranium for administration (personal communication).

Intrathecal infusions in human beings are commonly performed by surgically inserting a catheter at about the L4/L5 interspace and administering either (i) a bolus dose (via syringe or Ommaya reservoir), (ii) a short term infusion (via a pump), or (iii) a long term infusion (via an implantable programmable pump system, e.g. Synchromed II, Medtronic, where the pump is placed in a subcutaneous pocket somewhere in the body such as the abdominal region) (as described in Hamza et al. 2015). Further details for infusions can be found in Cook et al. 2009:

"Intrathecal agents can be administered into the lumbar cistern by means of a lumbar puncture. This is a routine medical procedure that has diagnostic and therapeutic roles for many CNS disorders. A spinal tap can be performed at the bedside with local anesthetic under sterile conditions. A spinal needle is advanced into the thecal sac through an interlaminar space in the lower lumbar spine. Access into the lumbar cistern is confirmed when CSF is obtained.

Drug delivery can be accomplished by injecting the drug through the spinal needle. The needle is then removed. This technique is used frequently for administration of chemotherapeutic drugs. Advantages of this technique include its relatively low risk and ability to be performed at the bedside under local anesthetic. The major disadvantage is that a separate puncture must be performed each time a dose is given, resulting in a cumulative risk of introducing infection, developing a cutaneous-CSF fistula, injuring nerve roots, and causing intraspinal hemorrhage. To circumvent this problem, a temporary indwelling catheter can be placed by using a similar technique with a larger Touhy needle.

The catheter is advanced into the thecal sac through the center of the needle, and the needle is subsequently withdrawn. The catheter is then tunneled subcutaneously through the skin where it can be accessed sterilely for scheduled doses of a chosen intrathecal drug. This technique is used often to perform a trial of response to therapy with intrathecal baclofen delivery for the treatment of spasticity and dystonia. The main disadvantages of this technique include the risk of infection with prolonged catheter placement and catheter malfunction from occlusion, kinking, or displacement. Most physicians would remove or replace the catheter after a few days."

The lateral ventricle can be directly accessed as well. Because of the concern for neurovascular injury and intracranial hemorrhage, repeated "taps" of the ventricle are not routinely performed. An exception to this rule might be in premature neonates who during pathologic conditions often have very large ventricles, a thin cortical mantle, and an open fontanelle, making the cumulative risks of repeated taps lower in this population.

In general, a permanent or temporary catheter-based device is implanted. For permanent access, a catheter that is connected to a subcutaneous reservoir is implanted. The most common type is an Ommaya reservoir. This reservoir can be accessed repeatedly at the bedside with a sterile puncture through the scalp into the reservoir by using a 25-gauge needle. Generally, a few milliliters of CSF is withdrawn before injecting the therapeutic agent.

This technique is ideal for conditions requiring long-term intraventricular drug administration such as carcinomatous meningitis or CNS lymphoma. Contamination and infection of the Ommaya reservoir is a risk, although less likely than with other methods of accessing the intraventricular compartment (approximately 10% of patients ultimately have CSF contaminated with bacteria). Infection rates often appear higher in case series reporting infectious complications with Ommaya reservoirs because of the duration of implantation (often >1 yr) compared with other more temporary access devices. Other rare complications that may occur with Ommaya reservoirs include leukoencephalopathy, white matter necrosis, and intracerebral hemorrhage.

In situations that require limited access to the CSF space, a ventriculostomy can be placed. With this technique, the catheter is tunneled under the skin away from the burr hole. The catheter is usually connected to a sterile collection chamber. The catheter can be accessed sterilely as needed for drug administration. Drugs may be administered by injecting the solution into the most proximal port of the ventriculostomy and flushing the solution into the brain with a small amount of normal saline (3-5 ml). After this instillation, the ventriculostomy tubing is typically clamped for at least 15 minutes to allow for the injected solution to equilibrate in the CSF before reopening the drain. Patients with persistently elevated intracranial pressure may not tolerate the abrupt cessation of CSF drainage, so ventriculostomy clamping should be done with caution and close monitoring of the patient. A ventriculostomy is ideal for a condition that requires a limited time period for CSF drainage or intraventricular drug administration."

Volume to be Infused

Because the basis of the present invention is to add an osmolyte, such as mannitol or sorbitol, as an additive to an aqueous formulation containing an active agent, the invention logically utilizes the same volumes and concentration of active agents routinely used or envisioned without the co-infused osmolyte.

Pre-infusion of the osmolyte is envisioned within the scope of the invention. We envision that pre-infusion of an osmolyte within 6-7 hours or less before infusion of an active agent will provide a distribution advantage (6-7 hours is the turnover time of human CSF; Thorne. 2014).

We currently infuse 80 microliters over 50 minutes in the adult rat model. Adult rats weigh approximately 200-300 grams. Rats have a CSF volume of approximately 200-300 microliters (Thorne. 2014). Based on body weight, scaling up the infusion volume from the rat model to a 72 kg adult human would entail an infusion of 19.2-28.8 mL over 50 minutes. Adult human beings have a total CSF volume of approximately 140-150 mL (Thorne. 2014).

Based on CSF volumes, scaling up the infusion volume from the rat model to the human would entail an infusion of 40-56 mL over 50 minutes. Based on CSF production rates in the human (350-370 microliters/min) and the rat (2-5 microliters/min), scaling up the infusion volume from the rat model (1.6 microliters/min) to the human would yield a volumetric flow rate range of 118-280 microliters/min (or 5.9-14 mL over 50 min). Reasonable upper limits for CSF infusion volumes in the human based on the rat model and physiological/scaling considerations may therefore be in the range of 6-60 mL over 50 minutes. Practically, these could be higher or significantly lower based on neurosurgical experience with humans undergoing intrathecal or intraventricular drug infusions. The lower limit is difficult to define as certain implanted pumps could be envisioned to deliver much, much lower volumetric flow rates over days, weeks, months or even years (e.g. 0.2 microliters per hour or lower in humans; Thorne & Frey. 2001).

Timing/Flow Rates:

Timing and flow rates are expected to be extremely varied depending on the therapeutic. It would likely include a range from as frequently as dosing once or multiple times a day to as infrequently as a one-time dose administration, or be a constant/continuous (likely slow) infusion. For example, some indications (i.e., treatment of chronic pain) may require continual infusion of a therapeutic, where others (i.e., chemotherapy or lysosomal storage enzyme replacement therapy) may infuse every other week, and others (i.e., single dose gene therapy vector) may be infused only once.

One may wish to consult the Great Ormond Street Hospital (GOSH) Operational Policy for a step-by-step guide for intrathecal lumbar administration of chemotherapeutics.

For example, Ziconotide is found in 20 mL single use vials at a concentration of 25 µg/mL (to be used undiluted); at rates used in trials (not used clinically) of 0.1-7.0 µg/hr. This translates to infusion rates of 0.004-0.28 mL/hr Baclofen is administered first in "screening" as a bolus dose of 50 µg in 1 mL over 1 minute or greater. If first bolus does not produce sufficient response a second or third bolus dose can be administered (1.5 mL or 2 mL, presumably over >1.5 minutes or >2 minutes, respectively). Maintenance dosing ranges from 12 µg/day to 2003 µg/day, but most require between 300-800 µg/day. 800 µg/day (considering ampules contain concentration of 50 µg in 1 mL) would equate to an infusion rate of 16 mL/day or 0.67 mL/hr.

For example, Sophysa ports for intrathecal use include the Soph-A-Port Mini and Standard Spinal ports, which are currently in use for clinical trials of lysosomal storage disorders in children (Hunter, Sanfilippo A, and Metachromatic leukodystrophy). An example of an intrathecal pump, the Medtronic SynchroMed II Programmable Infusion Pump (Model 8637) may be used with an intrathecal catheter for pump access (Medtronic Ascenda Intrathecal Catheter Models 8780 and 8781 or 8731SC). Other examples include Codman 3000, Codman Archimedes, Medtronic IsoMed pump, Advanced Neuromodulation System/St. Jude Medical AccuRx pump with DuraCath intraspinal catheter, Braun Celsite Spinal Access port and the Solomon Scientific TuBo Epidural and intrathecal port.

REFERENCES CITED

Budavari, S. (1989). The Merck index: An encyclopedia of chemicals, drugs, and biologicals (11th ed., centennial ed.). Rahway, N.J., U.S.A.: Merck.

Calias, P., W. A. Banks, D. Begley, M. Scarpa, and P. Dickson. Intrathecal delivery of protein therapeutics to the brain: a critical reassessment. *Pharmacology & Therapeutics* 144:114-122 (2014).

Cook, A. M., K. D. Mieure, R. D. Owen, A. B. Pesaturo, and J. Hatton. Intracerebroventricular administration of drugs. *Pharmacotherapy* 29: 832-845 (2009).

Creighton, H., and D. Klauder. Solubility of mannite in mixtures of ethyl alcohol and water. *Journal of the Franklin Institute* 854-854 (1923).

Dayson, H. and M. B. Segal. Physiology of the CSF and blood-brain barriers. CRC Press, Boca Raton, Fla. 822 pages (1996).

Gabas, N., T. Carillon, and N. Hiquily. Solubilities of D-xylose and D-mannose in water-ethanol mixtures at 25° C. *J Chem Eng Data* 33: 128-130 (1988).

Gray, S. J., S. N. Kalburgi, T. J. McCown, and R. J. Samulski. Global CNS gene delivery and evasion of anti-AAV-neutralizing antibodies by intrathecal AAV administration in non-human primates. *Gene Therapy* 20:450-459 (2013).

Hammarlund-Udenaes, M., E. C. L. de Lange, and R. G. Thorne (Ed.). *Drug Delivery to the Brain: Physiological Concepts, Methodologies and Approaches*. Springer, New York. 731 pages (2014).

Hamza, Maged, MD*; Daniel M. Doleys, PhD†; Islam A. Saleh, MD‡; Andrew Medvedovsky, MD§; Michael H. Verdolin, MD¶; Monalyce Hamza, B A**. A Prospective, Randomized, Single-Blinded, Head-to-Head Long-Term Outcome Study, Comparing Intrathecal (IT) Boluses With Continuous Infusion Trialing Techniques Prior to Implantation of Drug Delivery Systems (DDS) for the Treatment of Severe Intractable Chronic Nonmalignant Pain. Neuromodulation (2015, in press).

Iliff, J. J., M. Wang, Y. Liao, B. A. Plogg, W. Peng, G. A. Gundersen, H. Benveniste, G. E. Vates, R. Deane, S. A. Goldman, E. A. Nagelhus, and M. Nedergaard. A paravascular pathway facilitates CSF flow through the brain parenchyma and the clearance of interstitial solutes, including amyloid β. *Science Transl Med* 4(147): 147ra111 (2012).

Iliff, J. J., H. Lee, M. Yu, T. Feng, J. Logan, M. Nedergaard, and H. Benveniste. Brain-wide pathway for waste clearance captured by contrast-enhanced MRI. *J Clin Invest* 123:1299-1309 (2013).

Lochhead, J. J., D. J. Wolak, M. E. Pizzo, and R. G. Thorne. Rapid transport within cerebral perivascular spaces underlies widespread tracer distribution in the brain after intranasal administration. *Journal of Cerebral Blood Flow and Metabolism* 35:371-381 (2015).

Mullin, J. W. (2001). *Crystallization* (4th ed.). Oxford: Butterworth-Heinemann.

Needham Jr., T. E., A. N. Patuta, and R. J. Gerraughty. Solubility of Amino Acids in Pure Solvent Systems. *J Pharm Sci* (1971).

Park, Won-Young, MD1, Han-Jo Kim, MD2, Kyoungha Kim, MD1, Sang-Byung Bae, MD, PhD2, Namsu Lee, MD, PhD', Kyu-Taek Lee, MD, PhD2, Jong-Ho Won, MD, PhD', Hee-Sook Park, MD, PhD1, Sang-Cheol Lee, MD, PhD2. Intrathecal Trastuzumab Treatment in Patients with Breast Cancer and Leptomeningeal Carcinomatosis. *Cancer Res Treat* (2015, in press).

Samaranch, L., E. A. Salegio, W. S. Sebastian, A. P. Kells, J. R. Bringas, J. Forsayeth, and K. S. Bankiewicz. Strong cortical and spinal cord transduction after AAV7 and AAV9 delivery into the cerebrospinal fluid of nonhuman primates. *Human Gene Therapy* 24:526-532 (2013).

Seidell, A. (1919). *Solubilities of inorganic and organic compounds c*. 2. D. Van Nostrand Company.

Speck., U., W.-R. Press, and W. Mutzel. Osmolality-related effects of injections into the central nervous system. *Invest Radiol* 23(Suppl 1):5114-5117 (1988).

Thorne, R. G. and W. H. Frey II. Delivery of neurotrophic factors to the central nervous system: Pharmacokinetic considerations. *Clinical Pharmacokinetics* 40 (12): 907-946 (2001).

Thorne, R. G., Hrabetova S., Nicholson C. Diffusion of Epidermal Growth Factor in Rat Brain Extracellular Space Measured by Integrative Optical Imaging. Journal of Neurophysiology 92:3471-3481 (2004).

Thorne, R. G. Primer on central nervous system structure/function and the vasculature, ventricular system and fluids of the brain. In: Drug Delivery to the Brain: Physiological Concepts, Methodologies and Approaches. Ed. Hammarlund-Udenaes, de Lange & Thorne. Springer, New York. Pages 685-707 (2014).

Wolak, D. J. and R. G. Thorne. Diffusion of macromolecules in the brain: implications for drug delivery. *Molecular Pharmaceutics* 10 (5):1492-504 (2013).

Wolak, D. J., M. E. Pizzo, and R. G. Thorne. Probing the extracellular diffusion of antibodies in brain using in vivo integrative optical imaging and ex vivo fluorescence imaging. *J Control Release* 197:78-86 (2015).

The invention claimed is:

1. A method of enhancing therapeutic/drug transport to perivascular spaces of a patient's brain, the method comprising the step of:
   injecting or infusing a therapeutic/drug and an osmolyte into a patient's cerebrospinal fluid (CSF), wherein the osmolyte is introduced to the CSF at a concentration between 0.5 M and 12.9 M (dependent on the solubility upper limit of the osmolyte), and wherein the therapeutic/drug delivery to the perivascular spaces of cerebral blood vessels and parenchyma in the patient's brain includes passing the therapeutic/drug through lining cells positioned on an external surface of the cerebral blood vessels, and wherein passing the therapeutic/drug through the lining cells is facilitated by the presence of the osmolyte, and wherein the injecting or infusing step is by way of intracerebroventricular injection or infusion, intrathecal intracisternal injection or infusion, or intrathecal lumbar injection or infusion.

2. The method of claim 1 wherein the osmolyte is introduced to the CSF at an osmolality between 600 mOsm/kg and 13 Osm/kg.

3. The method of claim 1 wherein the injection or infusion of the osmolyte and the therapeutic/drug is simultaneous.

4. The method of claim 1 wherein the osmolyte is injected or infused into the CSF before the therapeutic/drug.

5. The method of claim 1 wherein the therapeutic/drug and the osmolyte are infused at a volumetric flow rate between 1-60 mL per hour.

6. The method of claim 1 wherein the patient is a human.

7. The method of claim 1 where the therapeutic/drug is a macromolecule or biopharmaceutical with a Stokes-Einstein hydrodynamic diameter in the range of 1 to 15 nm.

8. The method of claim 1 where the therapeutic/drug is a macromolecule or biopharmaceutical with a Stokes-Einstein hydrodynamic diameter in the range of 15 to 300 nm.

9. The method of claim 1 where the therapeutic/drug is a macromolecule or biopharmaceutical with a Stokes-Einstein hydrodynamic diameter in the range of 15 to 800 nm.

10. The method of claim 1 where the therapeutic/drug is a macromolecule or biopharmaceutical with a Stokes-Einstein hydrodynamic diameter in the range of 10,000 to 30,000 nm.

11. The method of claim 1 where the therapeutic/drug is a macromolecule or biopharmaceutical is selected from the group consisting of a peptide, protein, antibody, RNA, asRNA, siRNA, DNA, cDNA, and viral vector.

12. The method of claim 1 where the therapeutic/drug is a stem cell.

13. The method of claim 1, where the therapeutic/drug is used to treat central nervous system diseases such as lysosomal storage disorders, primary and metastatic brain cancer, neurodegenerative disorders, stroke, multiple sclerosis, CNS infections, and traumatic injury of the brain or spinal cord.

14. The method of claim 1, where the therapeutic/drug is used to treat neurodegenerative disorders such as Alzheimer's, Parkinson's, Huntington's, amylotropic lateral sclerosis, and prion diseases.

15. The method of claim 1 wherein the therapeutic/drug is selected from a group consisting of those with a Stokes-Einstein hydrodynamic diameter of 1-10, 10-30, 30-100, 100-800, 800-10,000, and 10,000-30,000 nm.

16. A method of enhancing therapeutic/drug transport to perivascular spaces of a patient's brain, the method comprising the step of:

injecting or infusing a therapeutic/drug and an osmolyte into a patient's cerebrospinal fluid (CSF), wherein the osmolyte is selected from the group of mannitol and sorbitol and wherein the osmolyte is introduced to the CSF at an osmolality between 850 mOsm/kg and 4,200 mOsm/kg, and wherein the therapeutic/drug delivery to the perivascular spaces of cerebral blood vessels and parenchyma in the patient's brain includes passing the therapeutic/drug through lining cells positioned on an external surface of the cerebral blood vessels, and wherein passing the therapeutic/drug through the lining cells is facilitated by the presence of the osmolyte, and wherein the injecting or infusing step is by way of intracerebroventricular injection or infusion, intrathecal intracisternal injection or infusion, or intrathecal lumbar injection or infusion.

17. The method of claim 16 where the osmolyte is injected or infused to the CSF at a concentration between 0.5 and 1M.

18. The method of claim 16 where the osmolyte is introduced injected or infused to the CSF at an osmolality between 850 mOsm/kg and 2100 mOsm/kg.

* * * * *

UNITED STATES PATENT AND TRADEMARK OFFICE
CERTIFICATE OF CORRECTION

| | | |
|---|---|---|
| PATENT NO. | : 10,123,969 B2 | Page 1 of 1 |
| APPLICATION NO. | : 15/293925 | |
| DATED | : November 13, 2018 | |
| INVENTOR(S) | : Robert G. Thorne et al. | |

It is certified that error appears in the above-identified patent and that said Letters Patent is hereby corrected as shown below:

In the Specification

Column 1, Line 44, "Dayson" should be --Davson--.

Column 17, Line 7, "Dayson" should be --Davson--.

Column 18, Line 3, "5114" should be --S114--.

In the Claims

Column 20, Claim 18, Lines 20-21, "is introduced injected or" should be --is injected or--.

Signed and Sealed this
Sixteenth Day of July, 2019

Andrei Iancu
*Director of the United States Patent and Trademark Office*